United States Patent [19]  
Saingier et al.

[11] Patent Number: 4,695,641  
[45] Date of Patent: Sep. 22, 1987

[54] N-OXIRANEMETHANE N,N,N-TRIALKYLAMMONIUM COMPOUNDS

[75] Inventors: Jean Saingier, Wattrelos; Jean-Pierre A. Joly, Golbey, both of France

[73] Assignee: Dollfus-Meig & Cie, Paris, France

[21] Appl. No.: 788,810

[22] Filed: Oct. 18, 1985

Related U.S. Application Data

[62] Division of Ser. No. 605,393, Apr. 30, 1984, Pat. No. 4,582,917, which is a division of Ser. No. 493,560, Apr. 11, 1983, Pat. No. 4,652,267.

[30] Foreign Application Priority Data

Aug. 10, 1981 [FR] France ................. 81 15888  
Aug. 5, 1982 [FR] France ................. 82 00131

[51] Int. Cl.$^4$ ........................................... C07D 301/27  
[52] U.S. Cl. ........................................ 549/552; 8/188  
[58] Field of Search ................... 549/512, 551, 552

[56] References Cited

PUBLICATIONS

Chem. Abst., 66, 65384k, 1967.  
Chem. Abst., 87, 86710n, 1977.  
Chem. Abst., 99, 54515j, 1983.

*Primary Examiner*—Christopher Henderson  
*Attorney, Agent, or Firm*—Wenderoth, Lind & Ponack

[57] ABSTRACT

Compounds of the formula:

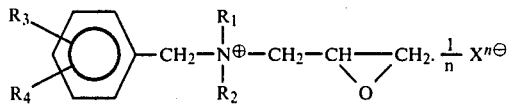

where  
$R_1$ is alkyl having 1 or 2 carbon atoms,  
$R_2$ is linear alkyl having 1 or 2, or from 12 to 16, carbon atoms,  
$R_3$ and $R_4$ are each chlorine or hydrogen, and  
$X^{n\ominus}$ is an anion, where n is the anion valence,  
with the proviso that $R_3$ and $R_4$ are not both hydrogen.

2 Claims, No Drawings

N-OXIRANEMETHANE N,N,N-TRIALKYLAMMONIUM COMPOUNDS

This application is a division of Ser. No. 605,393 filed Apr. 30, 1984, now U.S. Pat. No. 4,582,917, which is a division of Ser. No. 493,560 filed Apr. 11, 1983, now U.S. Pat. No. 4,652,267.

FIELD OF THE INVENTION

The present invention relates to salts of new derivatives of N-oxiranemethane N,N,N-trialkylammonium, their preparation method, their use in treatment of polyhydroxylated and polyaminated polymers so as impart to the polymers permanent bacteriostatic and/or fungistatic properties, and to the products thus treated.

More precisely, the compounds are used in the finishing of textile articles such as woven and knitted fabrics, nonwovens, cellulose based materials, for example in the form of cotton, viscose, rayon, polynosic, lin en, jute or ramie, or synthetic polymer based materials such as polyamides 6, 6/6, 11, aramides or cellulose acetates.

BACKGROUND OF THE INVENTION

For textile articles, such finished products could be obtained hitherto only temporarily by adjunction of cationic products, more or less substantive or direct at the moment of using the last rinsing bath.

Such a technique can lead to three major disadvantages:
the necessity of renewing the antimicrobial treatment at each washing,
a risk of insufficient penetration,
potential risks of intolerance and allergy for certain subjects.

It is well known that the textile materials form a vavourable medium for the development of microorganisms due to their porous and discontinuous structure. Textile fibres are in a fairly large proportion part of the modern environment: clothing, beddings, bathroom linen, hangings, lining of footwear, etc . . . . It is for this reason that researches have been carried out in order to impart to such articles permanent bacteriostatic and/or fungistatic properties, withstanding successive washing and sterilizing operations.

The method more currently used for avoiding the undesirable development of microorganisms in textile materials consists in carrying out a disinfection by the standard or dry cleaning method. It is known that washing with cold water alone is inefficient for destroying the noxious germs and that disinfecting baths are advocated even after boiling. Moreover, it proves that a frequent washing is not always possible in many cases, notably when it concerns articles used by military services in the field, personnel living in confined spaces such as hospitals, day-nurseries or hotels, or persons travelling extensively and for long periods. On the other hand, some textile articles such as blankets, tapestries, and curtains are irregularly and even never cleaned. Studies have demonstrated that such articles can accumulated a large quantity of germs, which are morbific and generators of unpleasant smells. Other works have demonstrated that noxious bacteria migrate easily from contaminated articles other others, during washing. The control of the bacterial development is of primary importance, not only with a prophylactic purpose but also for preventing the emergence of unpleasant smells.

SUMMARY OF THE INVENTION

The object of the present invention is to remedy such disadvantages and it relates, to this effect, to new salts derived from N-oxiranemethane N,N,N-trialkylammonium, of the general formula:

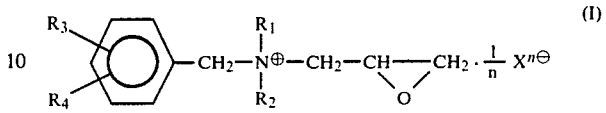

where
$R_1$ is an alkyl group having 1 or 2 carbon atoms,
$R_2$ is a linear alkyl group having 1 or 2, or from 12 to 16, carbon atoms,
$R_3$ and $R_4$ are each a chlorine or hydrogen atom, and
$X^{n\ominus}$ is an aion, where
n is X anion valence,
the methods for preparing such compounds, as well as a method for treating different textile materials by using the new compounds in order to impart to them permanent bacteriostatic and/or fungistatic properties, withstanding successive washing and sterilizing operations.

DETAILED DESCRIPTION OF THE INVENTION

The method for the treatment of textile materials by using the compounds hereabove defined is characterized in that the material to be treated is impregnated with a solution of one or several of the compounds, in a base such as soda, potash, sodium carbonate, sodium sodium trichloroacetate; the material treated is spin dried, and then stored protected from air for at least three hours.

According to an alternative embodiment of the method, the storage protected from air is replaced by a drying operation by any appropriate means, followed by a period where the material is kept at a temperature higher than 80° C.

The main interest of the treatment which is described in more detail hereafter resides in the permanency of the treatment by creating a covalent bond between the polymer and the salts of the derivatives of N-oxiranemethane N,N,N-trialkylammonium.

The second advantage deriving from the first is the harmlessness of the treatment due to the absence of salting-out during the life-time of the article.

The preparation method of the compound according to the invention is carried out in two stages. In a first stage, epichlorohydrin is reacted with a dialkylamine

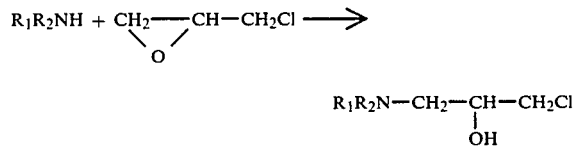

at a temperature from 30° to 35° C. in an aqueous medium. After cooling down to a temperature between 5° and 15° C., the concentration of OH⁻ ions is increased:

-continued

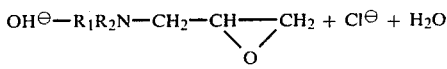

During the second stage, the product obtained at the end of the first stage is reacted with a compound of the formula:

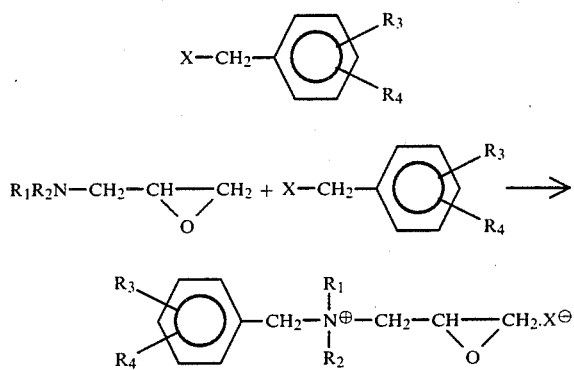

The reaction is carried out at room temperature in acetonitrile.

Anion $X^-$ can be an organic anion such as benzenesulphonate, p-toluenesulphonate, methulsulphonate, ethylsulphonate, acetate, methylsulphate, ethylsulphate and benzoate, or a mineral anion such as chloride, bromide, iodide, sulphate, phosphate or hydroxy. Indeed, it is well known to substitute, after the compound synthesis, one anion for another, in acetone as solvent.

As regards known preparation methods reference is made to the following articles:
H. GILMAN: J. Amer. Chem. Soc. 68, 1946, p 1291
KUWAMURA and
KAMEYAMA: Kogyo Kagaku Zasshi 67, 4 1964, p 592.

Among the compounds of the invention, the following can be cited in particular:
the chloride of N-benzyl N,N-dimethyl N-oxiramethane ammonium
the bromide of N-(2,6-dichlorobenzyl)N-dodecyl-N-methyl-N-oxirane methane ammonium
the bromide of N-(3,6-dichlorobenzyl)N-octyl N-methyl-N-oxiranemethane ammonium.

The textile material which is in the form of fibres, fluff, ribbon, sliver, yarns in a package or hank form, plyed or twisted yarns, sheet, film, flock, woven and knitted fabric, paper, or nonwoven, is subjected according to the invention to a series of treatments:

(a) an impregnation step with a solution of quaternary ammonium salt of the formula (I), the solution containing also a catalyst chosen from among the strong bases such as: NaOH, KOH, LiOH or the quaternary ammonium salt as such in the form of a hydroxide, at a concentration between 0.4 and 5% by weight and possibly a non-hydroxylated wetting agent.

Catalysts such as $Na_2CO_3$, $NaHCO_3$, $CCl_3CO_2{}^-Na^+$ are also usable, especially in the case of a subsequent thermosetting, (b) a squeezing out step so that there is left on the material only the quantity of salts of the hereabove formula corresponding to the desired nitrogen content in the final product of 0.05% to 0.5%, thereby imparting the desired bacteriostatic and fungistatic properties, (c) a thermosetting step after evaporation, at a temperature of 80°–140° C., which can be advantageously replaced by a maceration at room temperature and protected from air for 3 to 48 hours.

The invention will now be described in more detail with reference to hereafter non limiting examples:

EXAMPLE 1

Preparation of N,N-diethyl N-(epoxy 2,3-propyl)amine

To a mixture of 1.44 moles of diethylamine and 6 ml of water kept at 30°–35° is very slowly added, while being stirred, 1.464 moles of epichlorhydrin (135.4 g). The reaction is completed after 3 hr. (or when there is no more appreciable generation of heat).

The reaction mixture is then immediately cooled down to +4° C., then there is added thereto during 20 min. 144 g of soda at 50% (1.8 mole) while vigorously stirring. The emulsion is stirred for 20 extra min. at a temperature lower than 15° C.

360 ml of iced water are then added,. The organic phase is separated and the aqueous phase is extracted with 3 portions of ethyl ether (or $CCl_4$). The organic phases are reunited, dried on $MgSO_4$ (or on any other appropriate means), filtered, concentrated in vacuum, and finally distilled under argon at a reduced pressure.

The yield of the product is 62%.

IR film: $\nu_{epoxy}=1254\text{-}918\text{-}835\text{-}760$ cm$^{-1}$

This compound can be stored protected from air (under argon) and from light at 0° C., without alteration.

EXAMPLE 2

Preparation of N-dodecyl N-methyl N(epoxy 2,3-propyl)amine

To a dispersion of 0.105 mole of epichlorhydrin (9.72 g) and 0.01 mole of water kept at 35° C. is very slowly added 0.1 mole of monomethyldodecylamine (19.94 g). After a 2 hour reaction, the mixture is cooled down to +5° C. and 12 g. of soda at 50% (0.15 mole) are added for a period of 20 min. while vigorously stirring, and the stirring is continued for 40 min. after the end of the addition. The temperature is kept below 15° C. The organic phase is separated by decantation, filtered on Cellite and dried on $MgSO_4$.

The amine is purified by distillation under argon at a reduced pressure in a column of 8 cm without packing.

The yield of the product is 78%.

IR film: $\nu_{epoxy}=1257\text{-}930\text{-}833\text{-}768$ cm$^{-1}$.

The storage of this product is possible for several months when protected from light, at 0° C. under argon.

EXAMPLE 3

(a) In example 2, the monomethyldodecylamine is replaced by monomethylduododecylamine for obtaining the corresponding final product.

(b) In example 2, the monomethyldodecylamine is replaced by monomethylhexadecylamine for obtaining the corresponding final product.

EXAMPLE 4

Alkylation of the tertiary amines obtained according to examples 1 to 3.

10 mmoles of epoxylated tertiary amines and 10 mmoles of the chosen benzylic bromide are dissolved in 10 ml of acetonitrile at room temperature and kept for 16–72 hours while being stirred, protected from air. After this period, 30 ml of anhydrous ether are added in order to complete, if necessary the precipitation of gum obtained. The salts were rapidly spin dried and washed on a frit with 30 ml of anhydrous ether; the gums were mixed and washed with 30 ml of anhydrous ether under argon, then left in a strong vacuum for at least 2 hours at 35°–40° C.; p $< 1,33.10^{-2}$ mbar.

In the following Table are shown the starting tertiary amines, the alkylation agents used, the duration of the reaction, the yields and the epoxy rates. The last expression means, the fraction of molecule which is not hydrolyzed in the form of epoxide, as opposed to the hydrolyzed form in the form of glycol. (see: Durbetaki A. J. Anal Chem 28, 12, 1956, p 2000).

100° C., the fabric is subjected to a thermosetting operation for 2 min. at 140° C. After rinsing with cold water the material can be bleached, preferably with chlorite then dried.

Such a fabric exhibits a real and permanent bacteriostatic activity as regards Staphylococcus, Streptococcus or Pneumococcus microorganisms.

We claim:

1. A compound of the formula:

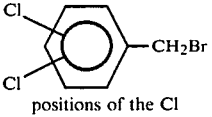

TABLE

| Tertiary amine formula II $R_1$ and $R_2$ | Alkylation agent 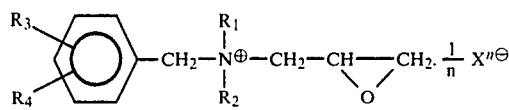 positions of the Cl | Duration (hr.) | Yield (%) | Epoxy rate (%) | Nature of product |
|---|---|---|---|---|---|
| $R_1 = R_2 = C_2H_5$ | 2.6 | 24 | 87 | 94 | |
| " | 2.5 | " | 90 | 97 | |
| " | 2.4 | " | 97 | 97 | crystallized salts |
| " | 3.4 | " | 92 | 98 | |
| " | 3.5 | " | 95 | 97 | |
| $R_1 = CH_3, R_2 = n\text{-}C_{12}H_{25}$ | without chlorine | " | 98 | 94 | |
| " | 2.6 | " | 97 | 95 | gums |
| " | 2.4 | " | 97 | 94 | |
| $R_1 = CH_3, R_2 = n\text{-}C_{14}H_{29}$ | without chlorine | " | | | |
| " | 2.6 | " | undetermined | | |
| $R_1 = CH_3, R_2 = n\text{-}C_{16}H_{33}$ | without chlorine | " | | | gums |
| " | 2.6 | " | | | |

EXAMPLE 5

A raw cotton fabric is subjected to padding at room temperature by using an aqueous solution containing:

60 g/l of chloride of N-benzyl N,N-dimethyl N-oxiranemethane ammonium 5 g/l of NaOH 3 g/l of an appropriate wetting agent such as the cottoclarin OK ® of Henkel.

The fabric is then squeezed out so as to leave on the material 80% of its weight in solution. After drying at where $R_1$ is alkyl having 1 or 2 carbon atoms, $R_2$ is linear alkyl having from 12 to 16, carbon atoms, $R_3$ and $R_4$ are each chlorine or hydrogen, and $X^{n\ominus}$ is an anion, where n is the anion valence, with the proviso that $R_3$ and $R_4$ are not both hydrogen.

2. A compound according to claim 1, wherein $R_3$ and $R^4$ are each chlorine.

* * * * *